(12) United States Patent
Silver et al.

(10) Patent No.: US 8,262,667 B1
(45) Date of Patent: Sep. 11, 2012

(54) MULTI-DIAMETER IMPLANT FORCEPS

(75) Inventors: William J. Silver, Grafton, MA (US); Luis A. Sousa, Cranston, RI (US)

(73) Assignee: Holmed Corporation, South Easton, MA (US)

( * ) Notice: Subject to any disclaimer, the term of this patent is extended or adjusted under 35 U.S.C. 154(b) by 1235 days.

(21) Appl. No.: 12/036,771

(22) Filed: Feb. 25, 2008

Related U.S. Application Data

(60) Provisional application No. 60/903,194, filed on Feb. 23, 2007.

(51) Int. Cl.
*A61B 17/00* (2006.01)
(52) U.S. Cl. .......................... 606/99; 606/207
(58) Field of Classification Search .............. 606/91, 606/99, 205–209; 623/19.11–19.14
See application file for complete search history.

(56) References Cited

U.S. PATENT DOCUMENTS

| | | | | |
|---|---|---|---|---|
| 1,980,477 A * | 11/1934 | Ertola et al. | .................... | 30/326 |
| D160,375 S * | 10/1950 | Edlund | .......................... | D7/686 |
| 4,676,798 A * | 6/1987 | Noiles | ........................ | 623/22.18 |
| 4,686,971 A * | 8/1987 | Harris et al. | .................... | 606/99 |
| 4,865,609 A * | 9/1989 | Roche | ........................ | 623/23.11 |
| 4,936,848 A | 6/1990 | Bagby | | |
| 5,070,623 A * | 12/1991 | Barnes | ............................ | 33/807 |
| 5,122,130 A | 6/1992 | Keller | | |
| 5,133,765 A * | 7/1992 | Cuilleron | ......................... | 606/89 |
| 5,264,680 A * | 11/1993 | Seibold et al. | ................ | 219/227 |
| 5,776,075 A * | 7/1998 | Palmer | .......................... | 600/564 |
| 5,913,858 A | 6/1999 | Calandruccio et al. | | |
| 6,478,822 B1 | 11/2002 | Leroux et al. | | |
| 6,585,771 B1 * | 7/2003 | Buttermilch et al. | ....... | 623/22.12 |
| 7,678,150 B2 * | 3/2010 | Tornier et al. | .............. | 623/19.13 |
| 7,828,806 B2 * | 11/2010 | Graf et al. | ........................ | 606/91 |
| 7,879,042 B2 * | 2/2011 | Long et al. | ...................... | 606/99 |
| 2004/0193278 A1 * | 9/2004 | Maroney et al. | ............ | 623/19.14 |
| 2007/0244563 A1 * | 10/2007 | Roche et al. | ................ | 623/19.12 |

OTHER PUBLICATIONS

Calandruccio, J. H., MD and M.T. Jobe, MD, "Orthosphere: Spherical Interpositional Implant," Surgical Technique, Wright Medical Technology, Inc, 2005, 12 pages.
"Delta CTA Reverse Shoulder Prosthesis," Surgical Technique, DePuy International Ltd., Aug. 2004, 28 pages.

* cited by examiner

*Primary Examiner* — Kevin T Truong
*Assistant Examiner* — Christopher Beccia
(74) *Attorney, Agent, or Firm* — Cesari and McKenna, LLP

(57) ABSTRACT

In one embodiment, a surgical instrument is provided for grasping spherical implants. The surgical instrument includes a first lever arm having distal and proximate ends, as well as a second lever arm having distal and proximate ends. A first concave grasping cup is disposed at the distal end of the first lever arm. A second concave grasping cup is disposed at the distal end of the second lever arm. The first grasping cup and the second grasping cup are of differing sizes to enable the instrument to securely grasp spherical implants of a plurality of differing sizes.

18 Claims, 6 Drawing Sheets

MULTI-DIAMETER IMPLANT FORCEPS

CROSS-REFERENCE TO RELATED APPLICATION

The present application claims the benefit of U.S. Provisional Patent Application Ser. No. 60/903,194, which was filed on Feb. 23, 2007, for Multi-Diameter Implant Forceps, and is hereby incorporated by reference in its entirety.

BACKGROUND

1. Technical Field

The present disclosure relates generally to surgical instruments and more specifically to surgical instruments for grasping spherical implants.

2. Background Information

Orthopedic surgeons may treat acute, chronic or traumatic injuries to the musculoskeletal system by replacing or augmenting injured structures with orthopedic prostheses and implants. For example, a surgeon may replace damaged or degenerated joints of the shoulder, hip, knee, elbow, or hand with a joint-replacement prosthesis, to reduce pain and improve mobility of a patient. Such treatment may be particularly appropriate when other treatment options have been exhausted.

Many joint-replacement prosthesis include a spherical implant that, together with a cup-like structure, form a ball and socket joint. As used herein, the term "spherical implant" should be interpreted broadly to encompass structures placed within the body that are shaped substantially as, or include a portion shaped substantial as, a hemisphere, a spherical cap, a sphere, a partial spheroid, a spheroid, or other similar three dimensional convex body. One specific type of a spherical implant is a glenosphere, which is commonly employed in reverse shoulder replacement surgery.

In a healthy shoulder, the humerus of the arm ends in a ball shaped humeral head, which fits into the socket-shaped scapula of the shoulder. In reverse shoulder replacement surgery, the anatomy is reversed. A ball-like structure is attached to the scapula and a socket is attached to the upper end of the humerus. In reference to the example reverse shoulder prosthesis 100 of FIG. 1, a portion of the humerus (not shown) is cut away and a diaphysis 110, a lower humeral stem, is inserted down the center of the humerus. An epiphysis 120, an upper portion humeral stem, is attached to the diaphysis 110 and also fits substantially within the humerus. The diaphysis 110 and epiphysis 120 are typically made of a hardened metal, such as titanium, cobalt chrome, or stainless steal. The epiphysis 120 holds a lateralised cup 130, typically made from polyethylene or another plastic material, which forms the socket of the new joint.

On the scapular side, a metaglene 140, a hardened metal plate, is attached to the scapula (not shown), typically with multiple bone screws 150. Finally, a spherical implant, in this case, a glenosphere 160, is affixed to the metaglene 140, typically by a central screw 170 or other fastener. The substantially hemispherically shaped glenosphere 160 fits inside the lateralised cup 130 to form the new shoulder joint. Both the glenosphere 160 and the lateralised cup 130 typically come in a variety of different sizes tailored to different body types and other factors. In some cases, size is an expression of diameter. Some common glenosphere diameters include 34 mm, 36 mm, 40 mm, and 42 mm.

When a spherical implant, such as a glenosphere 160, is employed, a surgeon must securely grasp the spherical implant to manipulate it into position and affix it in place. However, due to their curvature, spherical implants are typically quite difficult to grasp with many conventional surgical instruments. Some conventional surgical instruments may readily disengage (for example, slip from) a spherical implant. Other conventional surgical instruments, while better retaining a spherical implant, may damage the implant in the process, for example, by placing excessive pressure on a confined area of the implant, or by allowing the implant to rotate or move against portions of the instrument, which may lead to scratching.

The difficulties of grasping a spherical implant are further compounded by the existence of multiple sizes of spherical implants, for example multiple diameters of implants. Conventional instruments that may perform acceptably with a particular size spherical implant often fail completely, or perform quite poorly, with differently sized implants. Thus, if a surgeon desires the flexibility of using differently sized spherical implants, he or she typically must have on hand a range of different size-specific instruments. This both increases expense and creates logistical burdens.

Accordingly, there is a need for an improved surgical instrument that overcomes the shortcomings of prior designs.

SUMMARY

The shortcomings of the prior art are addressed in part by a novel surgical instrument having two grasping cups of differing sizes, that enables the instrument to securely grasp spherical implants of a plurality of differing sizes.

In an illustrative embodiment, the surgical instrument is a multi-diameter implant forceps. The multi-diameter implant forceps includes first and second lever arms coupled at a pivot, in an X-shaped arrangement. The proximate ends of the lever arms are gripped by a surgeon. The distal ends of the lever arms include grasping cups with concave interior surfaces to grasp a spherical implant. When placed about a spherical implant, the grasping cups surround at least a substantial portion of the implant. In the illustrative embodiment, the spherical implant is a glenosphere shaped substantially as a hemisphere, and the interior surface of each grasping cup is shaped substantially as a portion of a hemisphere.

To enable the forceps to grasp spherical implants of differing sizes, the first and second grasping cups are preferable differently sized. In the illustrative embodiment, grasping cup size is expressed in terms of a diameter of the enclosure formed by the interior surface of the grasping cup. The first grasping cup has a diameter approximately equal to the diameter of the smallest spherical implant the multi-diameter implant forceps is designed to grasp. The second grasping cup has a diameter approximately equal to the diameter of the largest spherical implant the multi-diameter implant forceps is designed to grasp. Such an arrangement enables the forceps to securely grasp the smallest diameter spherical implant, the largest diameter spherical implant, and all diameters in between. At a minimum, the grasping cups will contact a spherical implant at three differing points about their distal rims. In the most optimal case, the first smaller grasping cup will contact the spherical implant through 180° of arc along its distal rim, while the second larger grasping cup will contact, or nearly contact, the implant through roughly 90° of arc along its distal rim.

Various additional features may be employed to better retain a spherical implant in the grasping cups, prevent or minimize damage (e.g., scratches) to the implant, and/or provide other benefits. For example, in the illustrative embodiment, each grasping cup includes an under lip extending inward from its distal rim. The under lip engages a portion of a substantially flat underside of the spherical implant and prevents movement in a distal direction. Similarly, non-essential portions of each grasping cup may be "cut away" to create openings in the grasping cups, reducing the surface area in contact with the spherical implant to minimize damage. Further, a protective coating and/or finish may be added to the gasping cups to reduce damage (e.g., scratches). Coatings and/or finishes may include polymers (e.g., Polyethylene (PE) or Polytetrafluoroethylene, commonly marketed under the brand name Telfon®), luster (e.g., chrome), electro polish, or other types of materials or processes.

BRIEF DESCRIPTION OF THE DRAWINGS

The description below refers to the accompanying drawings, of which.

DETAILED DESCRIPTION OF AN ILLUSTRATIVE EMBODIMENT

Figure 1:
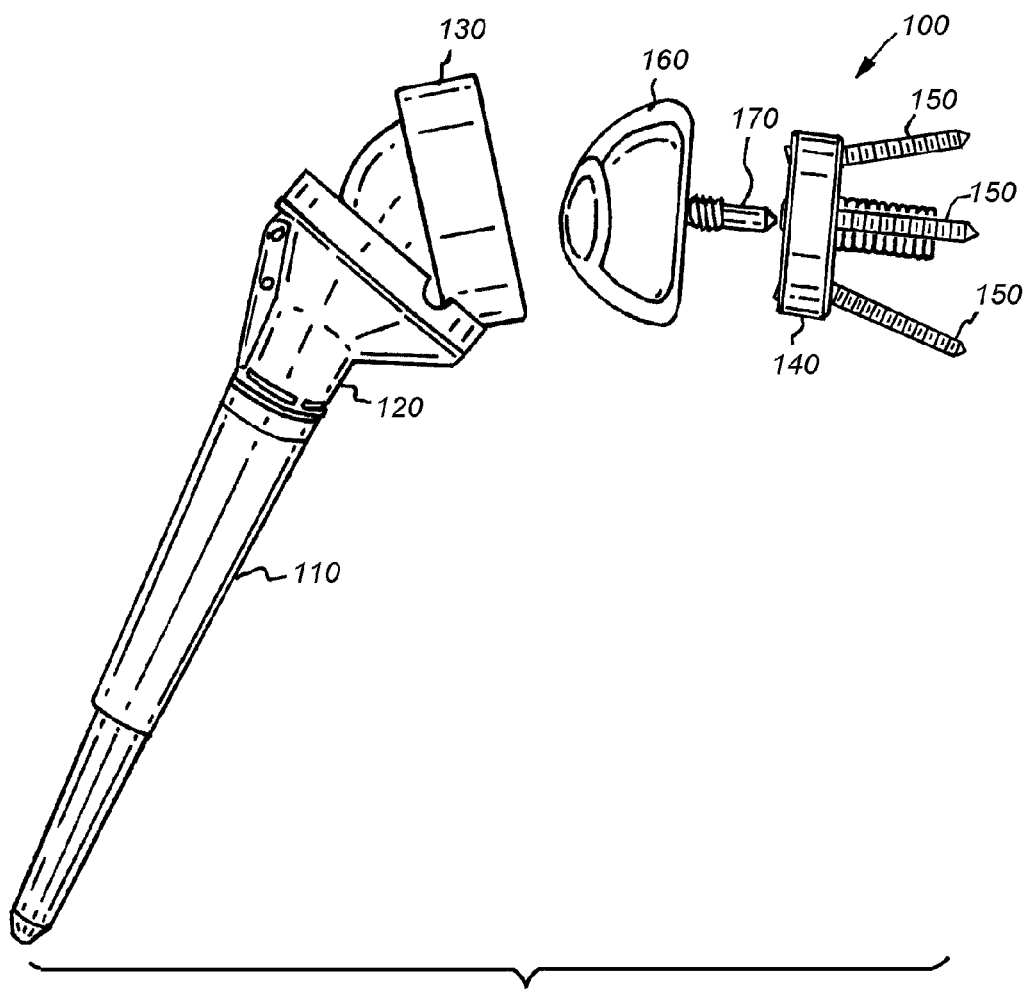
FIG. 1 is a schematic diagram of a reverse shoulder prosthesis including a spherical implant, according to the prior art.
Figure 2:
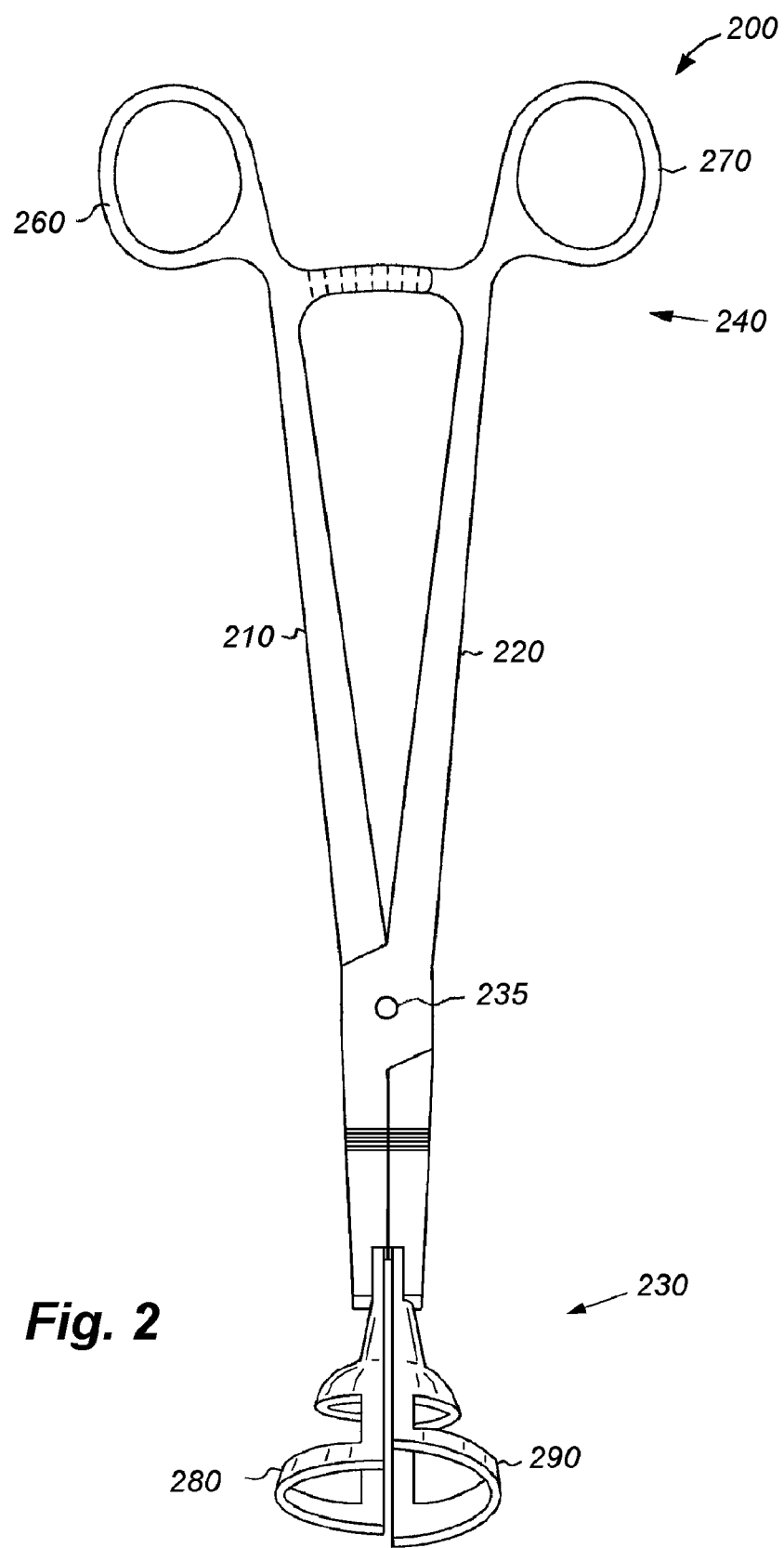
FIG. 2 is a first side view of an example multi-diameter implant forceps according to an illustrative embodiment of the present disclosure.
Figure 3:
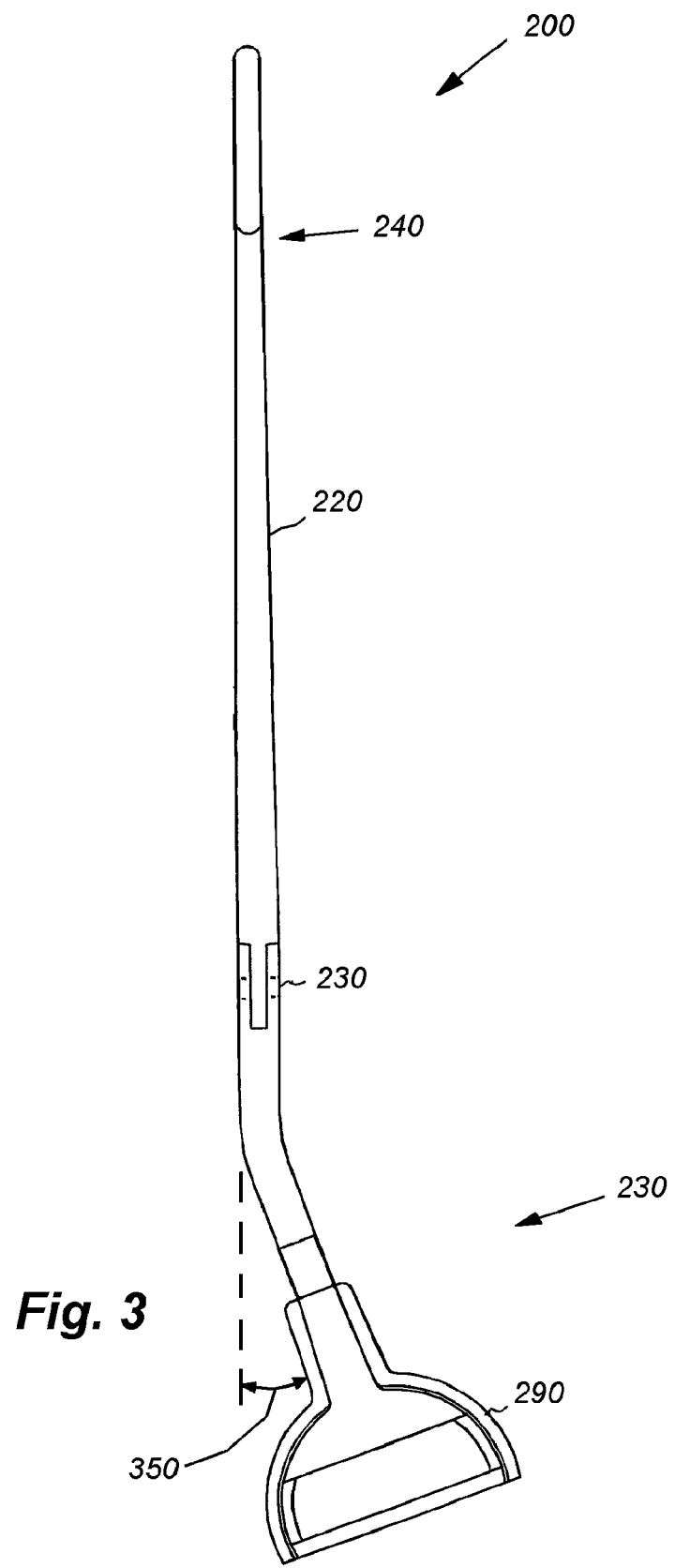
FIG. 3 is a second side view of the multi-diameter implant forceps.
Figure 4:
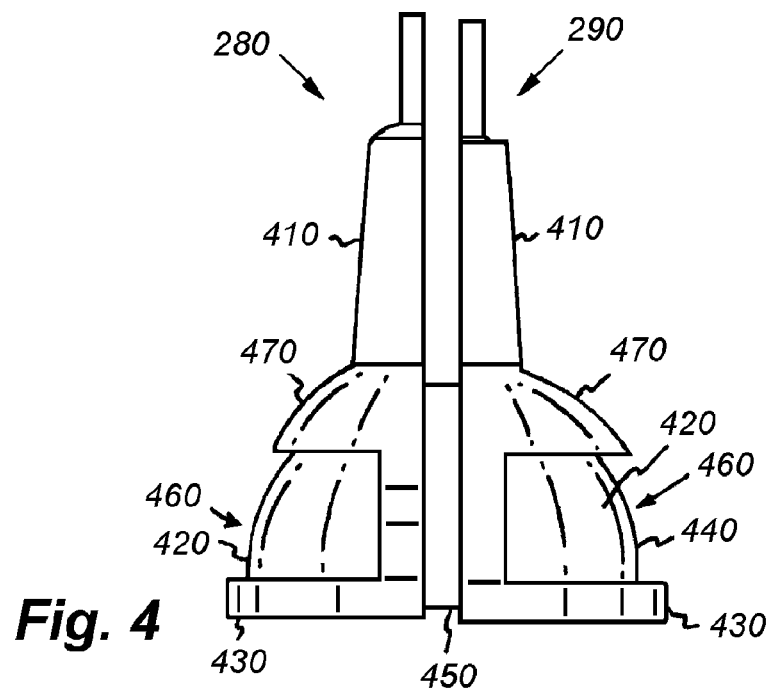
FIG. 4 is an enlarged side view of example grasping cups positioned about a spherical implant.
Figure 5:
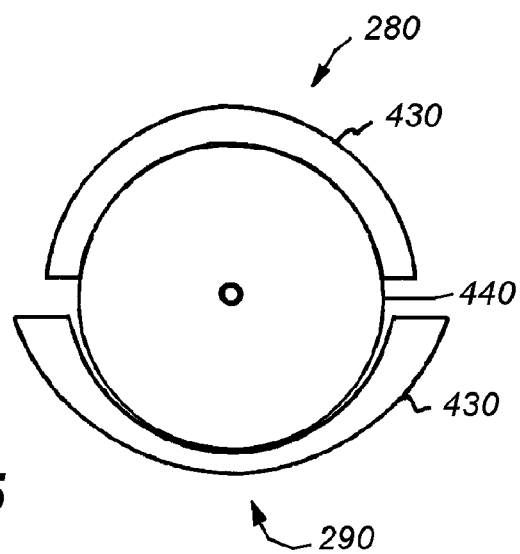
FIG. 5 is an enlarged bottom view of the grasping cups positioned about a spherical implant.
Figure 6:
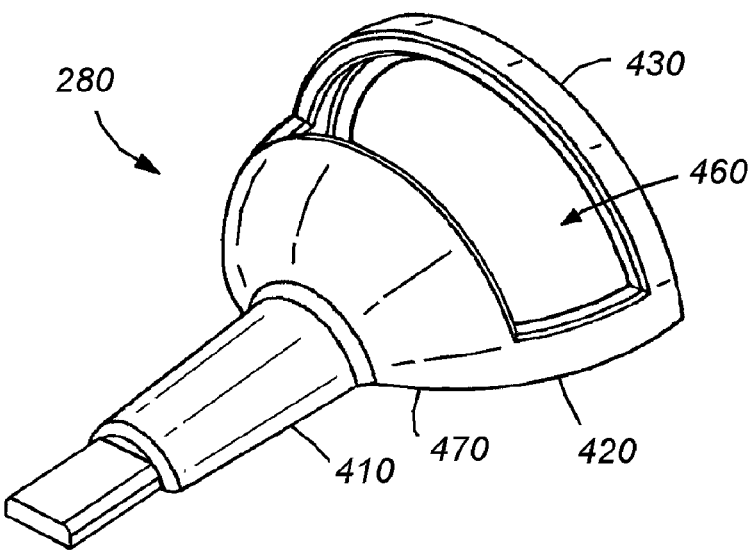
FIG. 6 is a first enlarged isometric view of a grasping cup.
Figure 7:
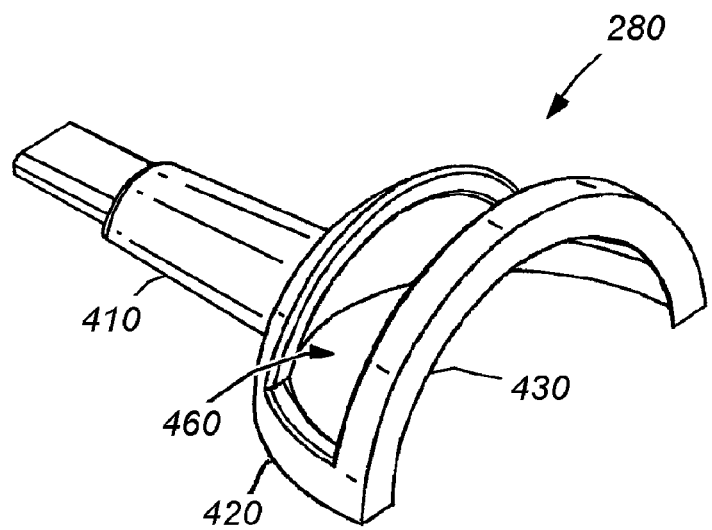
FIG. 7 is a second enlarged isometric view of a grasping cup.

In reference to FIG. 2 and FIG. 3, the example multi-diameter implant forceps 200 of the illustrative embodiment includes first and second lever arms 210, 220 coupled at a pivot 235, such as a bolt or rivet, in an X-shaped arrangement. The lever arms 210, 220 may be straight, or curved such that their distal ends 230 are offset from their proximate ends 240 by an angle 350. Such an offset may permit easier manipulation of an implant in a confined surgical space and accommodate the use of a guidewire. The proximate ends 240 of the lever arms 210,220 are designed to be gripped by a surgeon, and may include features to promote a secure grip, for example finger holes 260, 270 or finger contours (not shown). The distal ends 230 of the lever arms 210, 220 are designed to grasp a spherical implant with first and second grasping cups 280, 290. The grasping cups may be formed as integral parts of the first and second lever arms 210, 220, or may be separate components permanently, or removably coupled, to each lever arm 210, 220. For example, the grasping cups 280, 290 may be coupled to the via couplings, fasteners, adhesives, or other means depending on the particular implementation. The lever arms 210, 220 and the grasping cups 280, 290 of the example multi-diameter implant forceps 200 are preferably made from a metal, for example medical-grade stainless steal. However, a variety of other materials may be employed in alternate implementations, including plastics, composites, and combinations of multiple materials.

In reference to FIG. 4 through FIG. 7, further details of example grasping cups 280, 290 may be observed. Each grasping cup 280, 290 has a stem 410 at it proximate end, and a concave body 420 having interior and exterior surfaces, leading to a distal rim 430. In the illustrative embodiment, the spherical implant 440 is a glenosphere shaped substantially as a hemisphere. As such, in the illustrative embodiment, the interior surface of each grasping cup 280, 290 is shaped substantially as a portion of a hemisphere. It should be understood that in other embodiments both the spherical implant 440, and the grasping cups 280, 290, may be differently shaped. For example, the spherical implant 440 may be shaped substantial as a spherical cap, a sphere, a partial spheroid, a spheroid, or other similar three dimensional convex body. As appropriate for the shape of the spherical implant, the interior surface of each grasping cup grasping cups 280, 290 may be shaped as portions of spherical caps, portions of spheres, portions of spheroids, or other similar shapes such that they may surround at least a portion of the spherical implant 440.

To enable the forceps 200 to grasp a range of spherical implants 440 of differing sizes, the first and second grasping cups 280, 290 are preferable differently sized. In the illustrative embodiment, size is expressed in terms of a diameter of the enclosure formed by the interior surface of the grasping cups. In the illustrative embodiment, the first grasping cup 280 has a diameter approximately equal to the diameter of the smallest spherical implant 440 the forceps 200 is designed to grasp, for example a diameter of approximately 34 mm. The second grasping cup 290 has a diameter approximately equal to the diameter of the largest spherical implant 340 the forceps 200 is designed to grasp, for example a diameter of approximately 40 mm. Such an arrangement enables the forceps 200 to securely grasp the smallest diameter spherical implant, the largest diameter spherical implant and all diameters in between. At a minimum, when closed around a spherical implant 440, the grasping cups 280, 290 will contact the implant at three differing points about their distal rims 330. Such a minimal case occurs when the spherical implant has a diameter between that of the first grasping cup 280 and the second grasping cup 290. In the most optimal case, where the smallest diameter spherical implant is employed, the first smaller grasping cup 280 will contact the spherical implant 440 through the entire length of its distal rim 430, approaching about 180° of arc, while the second larger grasping cup 290 will contact, or nearly contact, the implant 440 through roughly 90° of arc along its distal rim 430. Thus, the grasping cups 280,290 of differing sizes are capable of securely grasping a range of differing size spherical implants.

Figure 8:
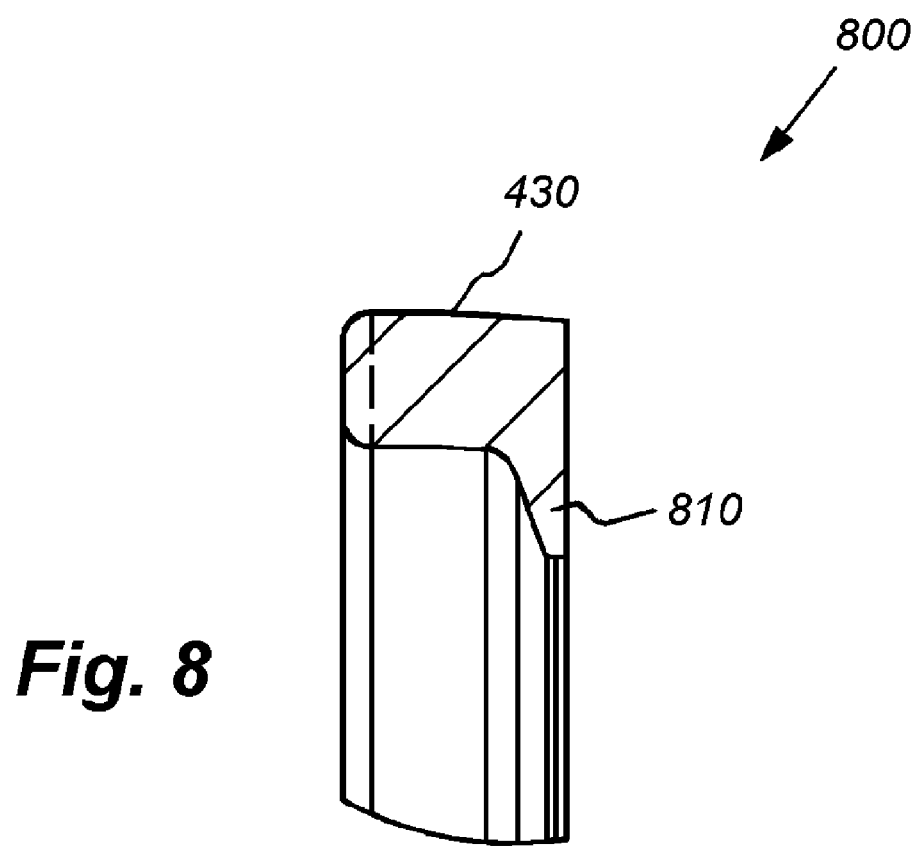
FIG. 8 is an enlarged cross-sectional view of a portion of the distal rim of a grasping cup.

Various additional features may be employed to better retain a spherical implant 440 in the grasping cups 280, 290, and to prevent or minimize damage thereto. FIG. 8 is an enlarged cross-sectional view 800 of a portion of the distal rim 430 of a grasping cup according to the illustrative embodiment. To help retain the spherical implant 440 in the grasping cup, the cup may include an under lip 810 extending inward from its distal rim 430. The under lip 810 is designed to engage the underside (FIG. 4, 450) of a spherical implant 440, to prevent movement of the implant in a distal direction.

Further non-essential portions of each grasping cup may be "cut away" to reduce surface area of the grasping cups 280, 290 in contact with the spherical implant 440. For example, in reference to FIG. 4, FIG. 6 and FIG. 7, openings 460 may be disposed in the grasping cups 280, 290. Reduced surface area in contact with the spherical implant 440 may minimize damage to the implant, for example may reduce scratching if the implant should happen to rotate or shift within the grasping cups 280, 290. The openings 460 may further reduce weight of the forceps 200, and allow better visibility of the implant 440 during a surgical procedure. While openings 460 may consume a substantial portion of grasping cups 280, 290, an inner cap region 470 about the proximate end of the grasping cups 280, 290 is preferably retained solid. The inner cap region 470 may support the implant 440 and prevent movement in a proximate direction.

In addition, a protective coating and/or finish may be added to the gasping cups to reduce damage (e.g., scratches). Coatings and/or finishes may include polymers (e.g., Polyethylene (PE) or Polytetrafluoroethylene, commonly marketed under the brand name Telfon®), luster (e.g., chrome), electro polish, or other types of materials or processes.

While the above description discusses an illustrative embodiment of present disclosure, it should be apparent that a number of modifications and/or additions may be made without departing from the disclosure's intended spirit and scope.

For example, while the illustrative embodiment involves an implant forceps, it should be understood that the teachings provided herein are broadly applicable, and may be used with a variety of types of surgical instruments other types of grasping devices.

Further, while in the illustrative embodiment size is expressed in terms diameter of the spherical implant 440 and of the enclosure formed by the interior surfaces of the grasping cups 280, 290, it should be understood that size may alternately be an expressions of other characteristics of three-dimensional shape. For example, size may be an expression of depth, height, curvature, or any of a variety of other characteristics. In such alternate cases, diameter may remain constant while other characteristics vary.

In addition, while mention is made above of reverse shoulder replacement surgery and other joint replacement uses of spherical implants, it should be understood that spherical implants have many possible applications, and may be employed in a variety of other types of surgical procedures. For example, spherical implants may serve as spinal implants to stabilize vertebra during spinal surgery. Accordingly, devices incorporating the teachings presented herein may be of use in a variety of different types of procedures.

Therefore, it should be understood that the above descriptions are meant to be taken only by way of example.

What is claimed is:

1. A surgical instrument for grasping spherical implants comprising:
   a first lever arm having distal and proximate ends;
   a second lever arm having distal and proximate ends;
   a first grasping cup disposed at the distal end of the first lever arm, the first grasping cup having a concave interior surface shaped substantially as a portion of a first hemisphere; and
   a second grasping cup disposed at the distal end of the second lever arm, the second grasping cup having a concave interior surface shaped substantially as a portion of a second hemisphere;
   wherein the first grasping cup and the second grasping cup are of differing sizes to enable grasping of spherical implants of a plurality of differing sizes.

2. The surgical instrument of claim 1 wherein the interior surface of the first and second grasping cups form enclosures of differing diameters.

3. The surgical instrument of claim 2 wherein the first grasping cup has a diameter approximately equal to the diameter of a smallest spherical implant the surgical instrument is to support and the second grasping cup has a diameter approximately equal to the diameter of a largest spherical implant the surgical instrument is to support.

4. The surgical instrument of claim 1 wherein at least one of the first and second grasping cups has a distal rim that includes an inward extending under lip.

5. The surgical instrument of claim 1 wherein at least one of the first and second grasping cups has an opening disposed therein, the opening reducing surface area in contact with a spherical implant.

6. The surgical instrument of claim 1 wherein at least one of the first and second grasping cups is covered with a protective coating or finish to reduce scratching of a spherical implant.

7. The surgical instrument of claim 1 wherein the first and second grasping cups are removably coupled to the respective first and second lever arms.

8. The surgical instrument of claim 1 wherein the first and second lever arms and the first and second grasping cups are constructed substantially of stainless steel.

9. The surgical instrument of claim 1 wherein the spherical implants are glenospheres of a reverse shoulder prosthesis.

10. The surgical instrument of claim 1 wherein the surgical instrument is a forceps and the first and second lever arms are coupled at a pivot.

11. A surgical instrument for grasping spherical implants comprising:
    a first grasping cup having a concave interior surface shaped substantially as a portion of a first hemisphere, the surface establishing an enclosure of a first diameter approximately equal to the diameter of a smallest spherical implant of a range of spherical implants supported by the instrument; and
    a second grasping cup having a concave interior surface shaped substantially as a portion of a second hemisphere, the surface establishing an enclosure of a second diameter approximately equal to the diameter of a largest spherical implant of a range of spherical implants supported by the instrument.

12. The surgical instrument of claim 11 wherein the first grasping cup is coupled to a first lever arm and the second grasping cup is couple to a second lever arm.

13. The surgical instrument of claim 12 wherein the surgical instrument is a forceps and the first and second lever arms are coupled at a pivot.

14. The surgical instrument of claim 11 wherein at least one of the first and second grasping cups has a distal rim that includes an inward extending under lip.

15. The surgical instrument of claim 11 wherein at least one of the first and second grasping cups has an opening disposed therein, the opening reducing surface area in contact with a spherical implant.

16. The surgical instrument of claim 11 wherein at least one of the first and second grasping cups is covered with a protective coating or finish to reduce scratching of a spherical implant.

17. The surgical instrument of claim 11 wherein the first and second lever arms and the first and second grasping cups are constructed substantially of stainless steel.

18. The surgical instrument of claim 11 wherein the spherical implants are glenospheres of a reverse shoulder prosthesis.

* * * * *